United States Patent
Kim et al.

(10) Patent No.: US 7,162,301 B2
(45) Date of Patent: Jan. 9, 2007

(54) METHOD AND SYSTEM FOR DETECTING CAPTURE WITH CANCELLATION OF PACING ARTIFACT

(75) Inventors: Jaeho Kim, Redmond, WA (US); Joseph Bocek, Seattle, WA (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 432 days.

(21) Appl. No.: 10/335,534

(22) Filed: Dec. 31, 2002

(65) Prior Publication Data
US 2004/0127949 A1    Jul. 1, 2004

(51) Int. Cl.
*A61N 1/37* (2006.01)
(52) U.S. Cl. .......................................... 607/28
(58) Field of Classification Search .............. 600/510; 607/9, 27–28
See application file for complete search history.

(56) References Cited

U.S. PATENT DOCUMENTS

| | | | |
|---|---|---|---|
| 4,825,869 A * | 5/1989 | Sasmor et al. ............... 607/27 |
| 5,033,473 A * | 7/1991 | Wang et al. ................. 600/509 |
| 5,350,410 A | 9/1994 | Kleks et al. |
| 5,697,957 A * | 12/1997 | Noren et al. ................. 607/28 |
| 6,038,474 A | 3/2000 | Zhu et al. |
| 6,101,416 A | 8/2000 | Sloman |
| 6,163,724 A | 12/2000 | Hemming et al. |
| 6,175,766 B1 | 1/2001 | Bornzin et al. |
| 6,188,928 B1 * | 2/2001 | Noren et al. ................. 607/28 |
| 6,418,343 B1 | 7/2002 | Zhang et al. |
| 2003/0050671 A1 * | 3/2003 | Bradley ....................... 607/27 |
| 2004/0127950 A1 | 7/2004 | Kim et al. |

* cited by examiner

*Primary Examiner*—Robert E. Pezzuto
*Assistant Examiner*—Kristen Mullen
(74) *Attorney, Agent, or Firm*—Hollingsworth & Funk, LLC

(57) ABSTRACT

Methods and systems for detecting capture using pacing artifact cancellation are described. One or more pacing artifact templates are provided and a cardiac signal is sensed in a cardiac verification window. Each of the pacing artifact templates may characterize the pacing artifact associated with a particular pacing energy level, for example. A particular pacing artifact template is canceled from the cardiac signal. Capture is determined using the pacing artifact canceled cardiac signal. Detection of fusion/pseudofusion beats may be accomplished by comparing a cardiac signal to a captured response template.

42 Claims, 13 Drawing Sheets

METHOD AND SYSTEM FOR DETECTING CAPTURE WITH CANCELLATION OF PACING ARTIFACT

FIELD OF THE INVENTION

The present invention relates generally to implantable medical devices and, more particularly, to verifying capture in the heart by detection of an evoked response following pacing.

BACKGROUND OF THE INVENTION

When functioning normally, the heart produces rhythmic contractions and is capable of pumping blood throughout the body. However, due to disease or injury, the heart rhythm may become irregular resulting in diminished blood circulation. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for providing electrical pulses to the heart. Leads extending into the patient's heart are connected to electrodes that contact the myocardium for sensing the heart's electrical signals and for delivering pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of pace pulses to the heart. Pace pulses are typically low energy electrical pulses timed to assist the heart in producing a contractile rhythm that maintains cardiac pumping efficiency. Pace pulses may be intermittent or continuous, depending on, the needs of the patient. There exist a number of categories of pacemaker devices, with various modes for sensing and pacing the heart.

When a pace pulse produces a contractile response in a heart, the contractile response is typically referred to as capture, and the electrical waveform corresponding to capture is denoted the evoked response. Superimposed with the evoked response may be a post pace residual polarization waveform. The magnitude of the post pace residual polarization waveform, denoted herein as the pacing artifact waveform, is affected by a variety of factors including lead polarization, after potential from the pace pulse, lead impedance, patient impedance, pace pulse width and pace pulse amplitude, for example.

A pace pulse must exceed a minimum energy value, or capture threshold, to produce a contraction. It is desirable for a pace pulse to have sufficient energy to stimulate capture of the heart without expending energy in excess of a capture threshold. Accurate determination of the capture threshold is required for efficient pace energy management. If the pace pulse energy is too low, the pace pulses may not reliably produce a contractile response in the heart resulting in ineffective pacing. If the pace pulse energy is too high, the result may be patient discomfort as well as shorter battery life.

Capture detection allows the cardiac rhythm management system to adjust the energy level of pace pulses to correspond to the optimum energy expenditure that reliably produces a captured response. Further, capture detection allows the cardiac rhythm management system to initiate a back-up pulse at a higher energy level whenever a pace pulse does not produce a captured response.

A fusion beat is a cardiac contraction that occurs when two intrinsic cardiac depolarizations of a particular chamber, but from separate initiation sites, merge. When the heart is being paced, a fusion beat may occur when an intrinsic cardiac depolarization of a particular chamber merges with a pacer output pulse within that chamber. Fusion beats, as seen on electrocardiographic recordings, exhibit various morphologies. The merging depolarizations of a fusion beat do not contribute evenly to the total depolarization.

Pseudofusion occurs when a pacer output pulse artifact is superimposed upon a spontaneous P wave during atrial pacing, or upon a spontaneous QRS complex during ventricular pacing. In pseudofusion, the pacing stimulus is ineffective because the tissue around the electrode has already spontaneously depolarized and is in its refractory period.

During normal pacing, the presence of fusion and pseudofusion beats may be of little consequence except for wasted energy due to the generation of unnecessary pace pulses. However, detection of fusion and pseudofusion beats may be required during an automatic capture or threshold determination procedures. Fusion and pseudofusion beats may cause false detection of capture and may lead to erroneous capture threshold values.

Capture may be verified by detecting a cardiac signal indicative of an evoked response. However, the evoked response must be discerned from the superimposed post pace residual polarization, denoted herein as a pacing artifact. In addition, fusion or pseudofusion beats may further obscure the evoked response. It is desirable to detect the evoked response and thereby verify capture so that an effective pace pulse energy may be chosen and appropriate back up pacing delivered.

For the reasons stated above, and for other reasons stated below which will become apparent to those skilled in the art upon reading the present specification, there is a need in the art for a method and device that reliably and accurately detects capture in a patient's heart by sensing an evoked response in the presence of the post pace residual polarization and possible fusion or pseudofusion beats. There exists a further need for such an approach that is adaptive and accommodates changes in the patient's capture threshold over time. The present invention fulfills these and other needs.

SUMMARY OF THE INVENTION

The present invention is directed to a method and device for detecting capture using pacing artifact cancellation. In accordance with one embodiment of the present invention, one or more pacing artifact templates are provided and a cardiac signal is sensed. A particular pacing artifact template is canceled from the cardiac signal. Capture is determined by analyzing the pacing artifact canceled cardiac signal.

In another embodiment of the invention, a method for detecting fusion/pseudofusion involves providing a captured response template. A cardiac signal is detected and the captured response template is canceled from the cardiac signal to form a captured response canceled cardiac signal. Fusion/pseudofusion is determined using the captured response canceled cardiac signal.

In a further embodiment of the invention, a medical device includes a lead system extending into the heart. The lead system includes electrodes positioned to detect cardiac signals. The lead system is coupled to sensing circuitry to sense the cardiac signals. The device further includes a pulse generator for producing pace pulses applied to the heart through the electrodes. A control system controls the operation of the device including the sense circuitry and the pulse generator. A capture detection system is coupled to the sensing circuitry and is configured to provide pacing artifact templates, cancel the pacing artifact template from the sensed cardiac signals, and determine if capture occurs using the pacing artifact canceled cardiac signal.

In a further embodiment of the invention, a system for detecting capture in a patient's heart includes means for providing one or more pacing artifact templates, means for sensing a cardiac signal, means for canceling a particular pacing artifact template from the cardiac signal, and means for determining if capture occurs using the pacing artifact canceled cardiac signal.

Another embodiment of the invention involves a system for detecting fusion/pseudofusion in a patient's heart. The system includes means for providing a captured response template, means for detecting a cardiac signal, means for canceling the captured response template from the cardiac signal to form a captured response canceled cardiac signal, and means for detecting fusion/pseudofusion using the captured response canceled cardiac signal.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
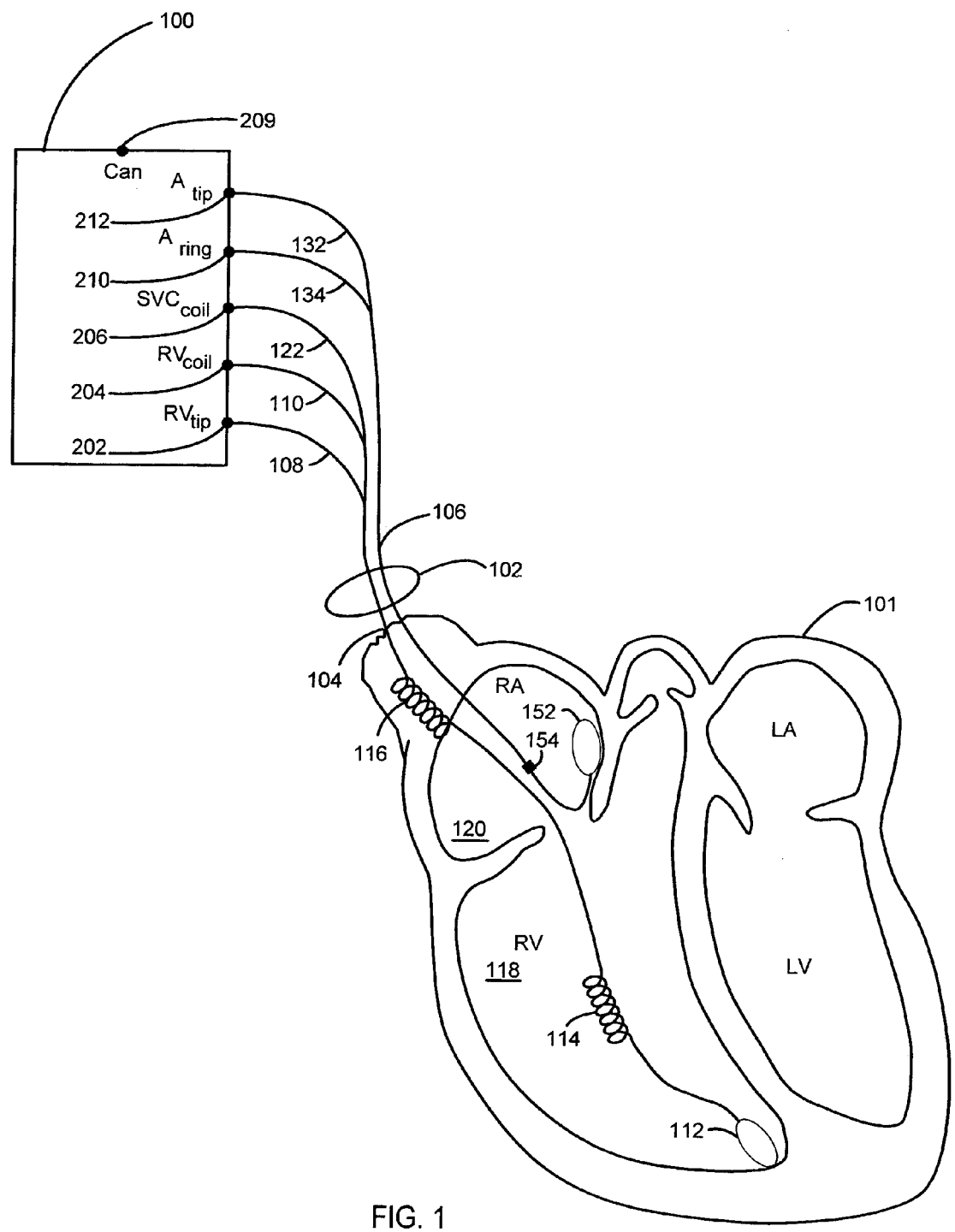
FIG. 1 is a partial view of one embodiment of an implantable medical device with an endocardial lead system extending into atrial and ventricular chambers of a heart.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

The embodiments of the present system illustrated herein are generally described as being implemented in an implantable cardiac defibrillator (ICD) that may operate in numerous pacing modes known in the art. Various types of single and multiple chamber implantable cardiac defibrillators are known in the art and may implement a capture verification methodology of the present invention. Furthermore, the systems and methods of the present invention may also be implemented in single and multi chamber pacemakers, resynchronizers, and cardioverter/monitor systems, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

The present invention provides a system and method for monitoring a patient's electrocardiogram and verifying that capture occurs following application of a pace pulse. Capture detection, along with fusion/pseudofusion detection, may be used, for example, in connection with an automatic capture verification procedure and the determination of the optimal energy of a pace pulse, such as in an automatic capture threshold procedure. Additionally, capture verification may be used on a beat-by-beat basis to control back-up pacing initiated when a pace pulse delivered to the heart fails to evoke a contractile response. These and other applications may be enhanced by employment of the systems and methods of the present invention.

Those skilled in the art will appreciate that reference to a capture threshold procedure indicates a method of measuring the stimulation threshold in either an atrium or a ventricle. In such a procedure, the pacemaker, automatically or upon command, initiates a search for the capture threshold of the chamber. In one example of an automatic capture threshold procedure, the pacemaker automatically decreases the pulse amplitude in discrete steps until a predetermined number of consecutive loss-of-capture events occur. At that point, the pacemaker may increase the stimulation voltage in discrete steps until a predetermined number of capture events occur to confirm the capture threshold. Various methods of implementing capture threshold procedures are known in the art and may be enhanced by the capture detection methods of the present invention.

Automatic capture threshold determination is distinguishable from automatic capture detection which is a procedure that occurs on a beat-by-beat basis. Automatic capture detection confirms on a beat-by-beat basis that a delivered pace pulse results in an evoked response. When no evoked response is detected following a pace pulse, the pacemaker may deliver a back up safety pulse to ensure consistent pacing. If a predetermined number of pace pulses delivered during normal pacing do not produce an evoked response, the pacemaker may initiate a capture threshold test as described above. The various procedures for implementing automatic capture detection and/or back up pacing processes may be enhanced by the capture detection methods described herein.

According to the present invention, a template of the pacing artifact is acquired or predicted by various methods. The pacing artifact template is canceled from a cardiac signal sensed following a pace pulse. Capture is determined using the pacing artifact canceled cardiac signal using various techniques. In one embodiment, capture detector circuitry determines capture has occurred by comparing an amplitude of the pacing artifact canceled cardiac signal to an amplitude associated with an evoked response. By this method, the pacing artifact canceled cardiac signal in a specified time window following the stimulation pulse is examined to determine if capture has occurred. If the pacing artifact canceled cardiac signal achieves the amplitude associated with an evoked response, the capture detector circuitry determines that capture has occurred.

In other embodiments, the capture detector may detect features of a pacing artifact canceled cardiac signal consistent with the morphology of an evoked response to determine capture. An exemplary set of features that may be used to determine capture include a slope of the cardiac signal, timing of local maxima or minima of the cardiac signal, or the rise time and/or fall times of the pacing artifact canceled cardiac signal. Other features of the pacing artifact canceled cardiac signal may also be used to determine if capture has occurred.

During a capture verification procedure, it may also be desirable to detect fusion and pseudofusion beats to prevent false capture detection. A method of detecting fusion/pseudofusion beats in accordance with the present invention relies upon canceling a template representative of a captured response from a sensed cardiac waveform and examining the resultant waveform. The captured response template includes two superimposed component signals, an evoked response and a pacing artifact response. The evoked response component represents the cardiac signal associated with contraction of the heart tissue in response to the pace pulse. The pacing artifact component represents the post pace residual polarization waveform. A fusion/pseudofusion beat may be discriminated from a captured response beat based on beat waveform morphology characteristics, as described in connection with capture detection above. For example, a fusion/pseudofusion beat may have a larger peak amplitude when compared to a captured response, allowing the fusion/pseudofusion beat to be detected.

Referring now to FIG. 1 of the drawings, there is shown one embodiment of a cardiac rhythm management system that includes an implantable cardiac defibrillator 100 electrically and physically coupled to an intracardiac lead system 102. The intracardiac lead system 102 is implanted in a human body with portions of the intracardiac lead system 102 inserted into a heart 101. The intracardiac lead system 102 is used to detect and analyze electrical cardiac signals produced by the heart 101 and to provide electrical energy to the heart 101 under certain predetermined conditions to treat cardiac arrhythmias, including, for example, ventricular fibrillation of the heart 101.

The intracardiac lead system 102 includes one or more pacing electrodes and one or more intracardiac defibrillation electrodes. In the particular embodiment shown in FIG. 1, the intracardiac lead system 102 includes a ventricular lead system 104 and an atrial lead system 106. The ventricular lead system 104 includes an SVC-coil 116, an RV-coil 114, and an RV-tip electrode 112. The RV-coil 114, which may alternatively be an RV-ring electrode, is spaced apart from the RV-tip electrode 112, which is a pacing electrode. In one embodiment, the ventricular lead system 104 is configured as an integrated bipolar pace/shock lead. In another exemplary configuration, one or more additional electrodes, e.g., a ring electrode, may be included in the ventricular lead system 104. The additional ring electrode and the RV-tip electrode 112 may be used for bipolar sensing of cardiac signals. The atrial lead system 106 includes an A-tip electrode 152 and an A-ring electrode 154. In one embodiment, the atrial lead system 106 is configured as an atrial J lead.

In this configuration, the intracardiac lead system 102 is positioned within the heart 101, with portions of the atrial lead system 106 extending into the right atrium 120 and portions of the ventricular lead system 104 extending into the right atrium 120 and right ventricle 118. In particular, the A-tip electrode 152 and A-ring electrode 154 are positioned at appropriate locations within the right atrium 120. The RV-tip electrode 112 and RV-coil 114 electrodes are positioned at appropriate locations within the right ventricle 118. The SVC-coil 116 is positioned at an appropriate location within the right atrium chamber 120 of the heart 101 or a major vein leading to the right atrium chamber 120 of the heart 101. The RV-coil 114 and SVC-coil 116 depicted in FIG. 1 are defibrillation electrodes.

Additional pacing and defibrillation electrodes may also be included in the intracardiac lead system 102 to allow for various bipolar sensing, pacing, and defibrillation capabilities. For example, the intracardiac lead system 102 may include endocardial pacing and cardioversion/defibrillation leads (not shown) that are advanced into the coronary sinus and coronary veins to locate the distal electrode(s) adjacent to the left ventricle or the left atrium. Other intracardiac lead and electrode arrangements and configurations known in the art are also possible and considered to be within the scope of the present system.

The ventricular and atrial lead systems 104, 106 include conductors for communicating sense, pacing, and defibrillation/cardioverter signals between the cardiac defibrillator 100 and the electrodes and coils of the lead systems 104, 106. As is shown in FIG. 1, ventricular lead system 104 includes a conductor 108 for transmitting sense and pacing signals between the RV-tip electrode 112 and an RV-tip terminal 202 within the cardiac defibrillator 100. A conductor 110 of the ventricular lead system 104 transmits sense signals between the RV-coil or ring electrode 114 and an RV-coil terminal 204 within the cardiac defibrillator 100. The ventricular lead system 104 also includes conductors 122 for transmitting sense and defibrillation signals between terminal 206 of the cardiac defibrillator 100 and the SVC-coil 116. The atrial lead system 106 includes conductors 132, 134 for transmitting sense and pacing signals between terminals 212, 210 of the cardiac defibrillator 100 and A-tip and A-ring electrodes 152 and 154, respectively.

Figure 2:
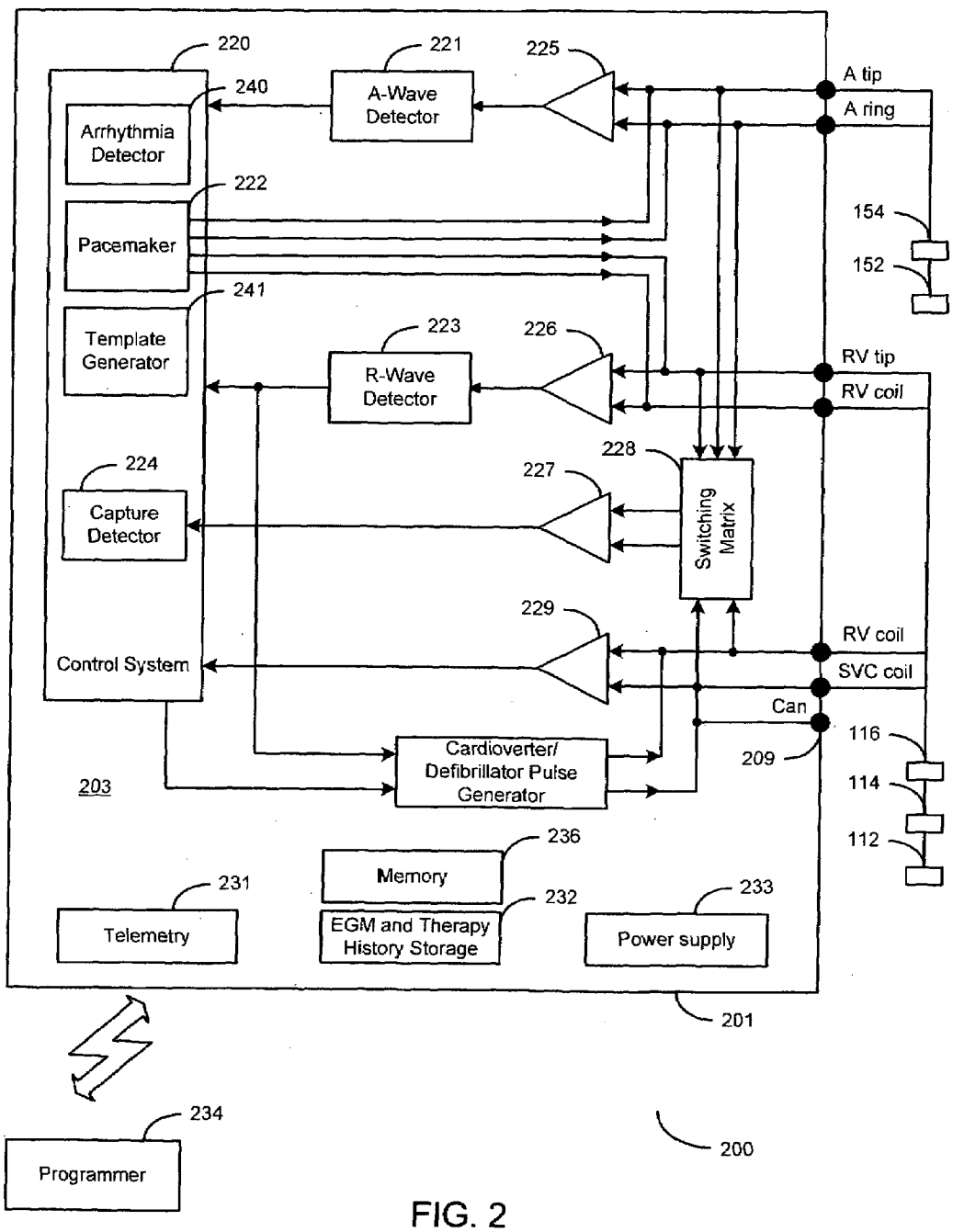
FIG. 2 is a block diagram of an implantable medical device with which capture verification and fusion/pseudofusion detection in accordance with the present invention may be implemented.

Referring now to FIG. 2, there is shown an embodiment of a cardiac defibrillator 200 suitable for implementing a capture verification methodology of the present invention. FIG. 2 shows a cardiac defibrillator divided into functional blocks. It is understood by those skilled in the art that there exist many possible configurations in which these functional blocks can be arranged. The example depicted in FIG. 2 is one possible functional arrangement. The cardiac defibrillator 200 includes circuitry for receiving cardiac signals from a heart 101 (not shown in FIG. 2) and delivering electrical energy to the heart. The cardiac defibrillator 200 includes terminals for connecting the cardiac defibrillator 200 to the electrodes of the intracardiac lead system as previously discussed.

In one embodiment, the cardiac defibrillator circuitry 203 of the cardiac defibrillator 200 is encased and hermetically sealed in a housing 201 suitable for implanting in a human body as is known in the art. Power to the cardiac defibrillator 200 is supplied by an electrochemical battery 233 that is housed within the cardiac defibrillator 200. A connector block (not shown) is additionally attached to the housing 201 of the cardiac defibrillator 200 to allow for the physical and electrical attachment of the intracardiac lead system conductors to the cardiac defibrillator 200 and the encased cardiac defibrillator circuitry 203.

In one embodiment, the cardiac defibrillator circuitry 203 of the cardiac defibrillator 200 is a programmable microprocessor-based system, including a control system 220 and a memory circuit 236. The memory circuit 236 stores parameters for various pacing, defibrillation, and sensing modes and stores data indicative of cardiac signals received by other components of the cardiac defibrillator circuitry 203. The control system 220 and memory circuit 236 cooperate with other components of the cardiac defibrillator circuitry 203 to perform operations involving the capture verification according to the principles of the present invention, in addition to other sensing, pacing and defibrillation functions. The control system 220 may encompass additional functional components including a pacemaker 222, an arrhythmia detector 240 and template generator 241 along with other functions for controlling the cardiac defibrillator circuitry 203. A memory 232 is also provided for storing historical EGM and therapy data. The historical data may be used for various purposes to control the operations of the cardiac defibrillator 200 and may also be transmitted to an external programmer unit 234 as needed or desired.

Telemetry circuitry 231 is additionally coupled to the cardiac defibrillator circuitry 203 to allow the cardiac defibrillator 200 to communicate with an external programmer unit 234. In one embodiment, the telemetry circuitry 231 and the programmer unit 234 use a wire loop antenna and a radio frequency telemetric link, as is known in the art, to receive and transmit signals and data between the programmer unit 234 and telemetry circuitry 231. In this manner, programming commands may be transferred to the control system 220 of the cardiac defibrillator 200 from the programmer unit 234 during and after implant. In addition, stored cardiac data pertaining to capture verification and capture threshold, along with other data, may be transferred to the programmer unit 234 from the cardiac defibrillator 200, for example.

Cardiac signals sensed through use of the RV-tip electrode 112 are near-field signals or rate channel signals as are known in the art. More particularly, a rate channel signal is detected as a voltage developed between the RV-tip electrode 112 and the RV-coil 114. Cardiac signals sensed through use of one or both of the defibrillation coils or electrodes 114, 116 are far-field signals, also referred to as morphology or shock channel signals, as are known in the art. More particularly, a shock channel signal is detected as a voltage developed between the RV-coil 114 and the SVC-coil 116. A shock channel signal may also be detected as a voltage developed between the RV-coil 114 and the can electrode 209. Alternatively, the can electrode 209 and the RV-coil electrode may be shorted and a shock channel signal sensed as the voltage developed between the RV-coil 114 and the can electrode 209 and SVC-coil 116 combination. Shock channel signals developed using appropriate combinations of the RV-coil, SVC-coil, and can electrodes 114, 116 and 209 are sensed and amplified by a shock EGM amplifier 229. The output of the EGM amplifier 229 is coupled to the control system 220.

In the embodiment of the cardiac defibrillator 200 depicted in FIG. 2, RV-tip and RV-coil electrodes 112, 114 are shown coupled to a V-sense amplifier 226 and thus to an R-wave detector 223. Rate channel signals received by the V-sense amplifier 226 are communicated to the R-wave detector 223, which serves to sense and amplify the rate channel signals, e.g. R-waves. The sensed R-waves may then be communicated to the control system 220.

A-tip and A-ring electrodes 152, 154 are shown coupled to an A-sense amplifier 225. Atrial sense signals received by the A-sense amplifier 225 are communicated to an A-wave detector 221, which serves to sense and amplify the A-wave signals. The atrial signals may be communicated from the A-wave detector 221 to the control system 220.

The pacemaker 222 communicates pacing signals to the RV-tip and A-tip electrodes 112 and 152 according to a preestablished pacing regimen under appropriate conditions. Blanking circuitry (not shown) is employed in a known manner when a ventricular or atrial pacing pulse is delivered, such that the ventricular channel, atrial channel, and shock channel are properly blanked at the appropriate time and for the appropriate duration.

A switching matrix 228, shown in FIG. 2, may be coupled to the A-tip 152, A-ring 154, RV-tip 112, RV-coil 114 and SVC-coil 116 electrodes. The switching matrix 228 may provide connections to various configurations of pacing and defibrillation electrodes, for example. The outputs of the switching matrix 228 are coupled to an ER amplifier 227 which serves to sense and amplify signals detected between the selected combinations of electrodes. The detected signals are coupled through the ER amplifier to a capture detector 224. The capture detector 224 includes circuitry configured to detect an evoked response and verify capture in accordance with the invention. The capture detector further includes circuitry for detecting fusion/pseudofusion beats.

Figure 3:
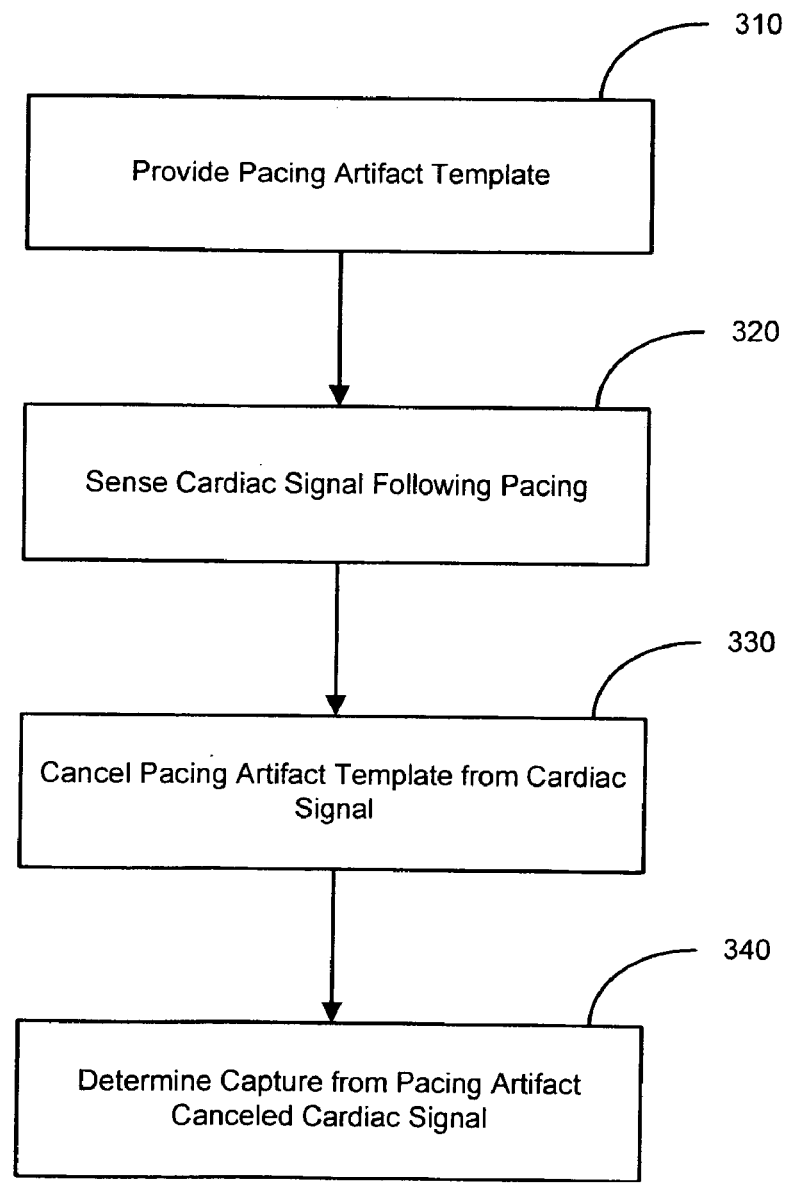
FIG. 3 is a flowchart conceptually illustrating a method of detecting capture in accordance with an embodiment of the present invention.

FIG. 3 is a flowchart illustrating various processes for capture verification according to an embodiment of the present invention. According to the embodiment illustrated in the flowchart of FIG. 3, upon commencement of capture verification, a pacing artifact template representative of post-pace residual polarization is provided 310. After a pace pulse is delivered, a resultant cardiac signal is sensed 320.

The pacing artifact template is canceled from the sensed cardiac signal 330. Capture is determined using the pacing artifact canceled cardiac signal 340.

Figure 4:
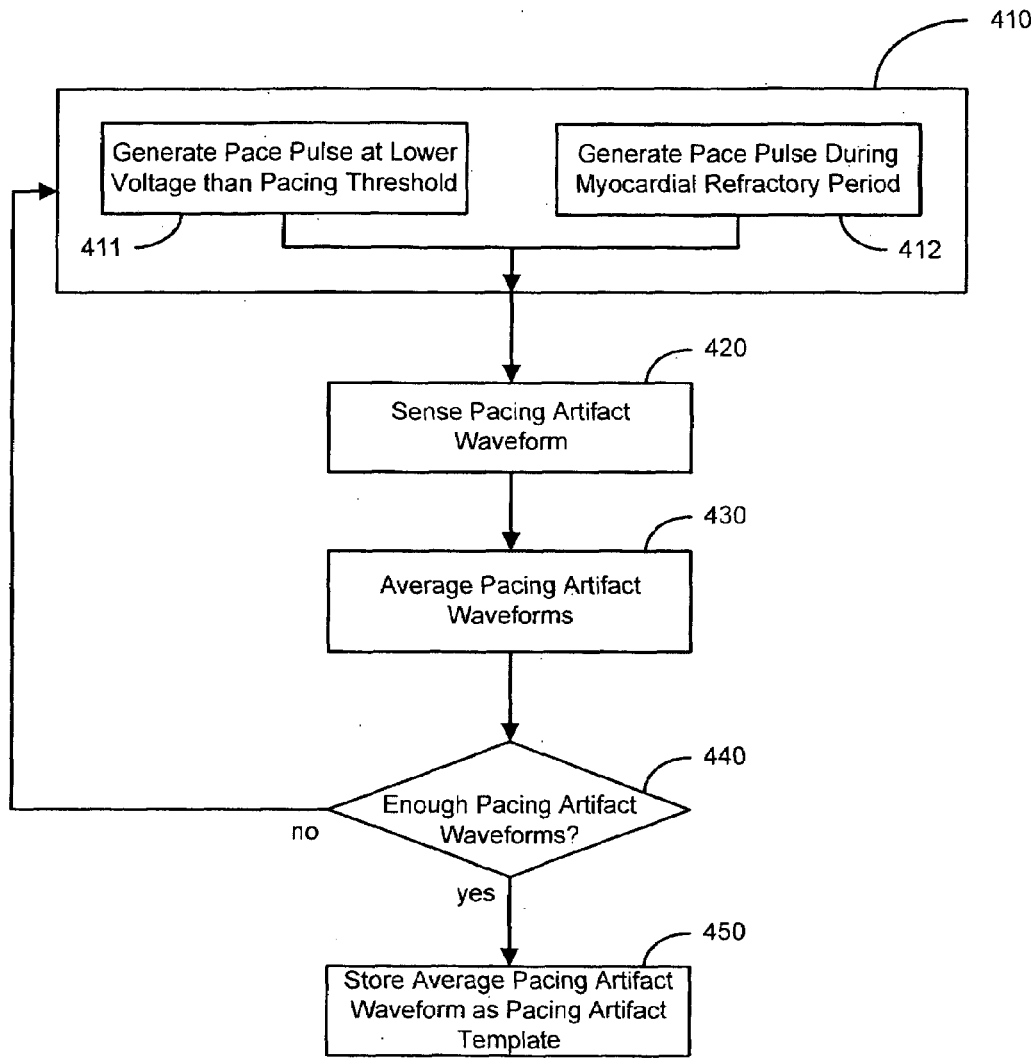
FIG. 4 is a flowchart illustrating a method of forming a pacing artifact template in accordance with an embodiment of the present invention.

FIG. 4 illustrates a method of generating a pacing artifact template according to another embodiment of the present invention. The method described in the following paragraph, with reference to FIG. 4, may be used to provide a pacing artifact template at blocks 310, 720, 1010, and 1305 in FIGS. 3, 7, 10, and 13, respectively. In the exemplary embodiment illustrated by FIG. 4, a pacing artifact template is formed through an iterative process. A number of pace pulses are delivered 410 to generate pacing artifact waveforms. The pace pulses are delivered in such a way that capture does not occur. The resultant cardiac signal represents a pure pacing artifact waveform without a superimposed evoked response. Pacing artifact signals without an associated evoked response may be produced by delivering 411 pace pulses at an energy level lower than the pacing threshold. Alternatively, the pace pulses may be delivered 412 during a myocardial refractory period. The myocardial refractory period represents a time when the heart tissue is recovering from a previous cardiac beat. Pace pulses delivered during the myocardial refractory period typically do not produce an evoked response in the heart tissue, thus a pure pacing artifact waveform may be acquired.

Following generation 410 of a pace pulse using either of the above methods described in connection with blocks 411 or 412, a pacing artifact waveform is sensed 420 during a cardiac verification window. For example, the cardiac verification window may begin approximately 25 ms after delivery of the pace pulse and continue for a time interval of approximately 50 ms. The pacing artifact waveform is averaged with previously acquired pacing artifact waveforms 430, if any. The process of generating a pace pulse and detecting the resultant pacing artifact waveform 410–430 is repeated until a predetermined number of pacing artifact waveforms has been acquired 440. When a sufficient number of pacing artifact waveforms has been acquired 440, the average pacing artifact waveform is stored 450 as the pacing artifact template.

The pacing artifact may exhibit small variations in morphology with respect to pace pulse amplitude. Accordingly, the use of multiple pacing artifact templates corresponding to various pace pulse amplitudes may provide a more thorough cancellation of the pacing artifact over a range of pace pulse amplitudes, e.g., as used in a pacing threshold test. The method illustrated in FIG. 4 can be applied to generate pacing artifact templates for each pacing pulse amplitude of interest.

Alternatively, or additionally, a set of two or more pacing artifact templates may be generated, wherein a particular pacing artifact template characterizes the pacing artifact associated with a small range of pace pulse amplitudes. A pacing artifact template for a pace pulse range can be formed by combining pacing artifact waveforms from various pace pulse amplitudes within the range using, for example, an averaging operation. The pacing artifact template for a pace pulse range may also be formed by selecting a pacing artifact waveform at a single pace pulse amplitude, e.g., a pacing artifact waveform for a pulse amplitude near the center of the range to be characterized. The set of pacing artifact templates correspond to the entire pace pulse amplitude range to be evaluated.

The artifact waveform measurement may be accomplished during the refractory period of the myocardium. Pace pulses delivered during the refractory period produce pacing artifact waveforms without the evoked response components. The timing of the pace pulse delivered for pacing artifact measurement in the myocardial refractory period should be selected to be before the vulnerable period of the myocardium to avoid pro-arrhythmia, and after the deflections from the myocardial response from the previous cardiac event in the chamber have passed, e.g., 80 ms after the preceding cardiac event.

Figure 5:
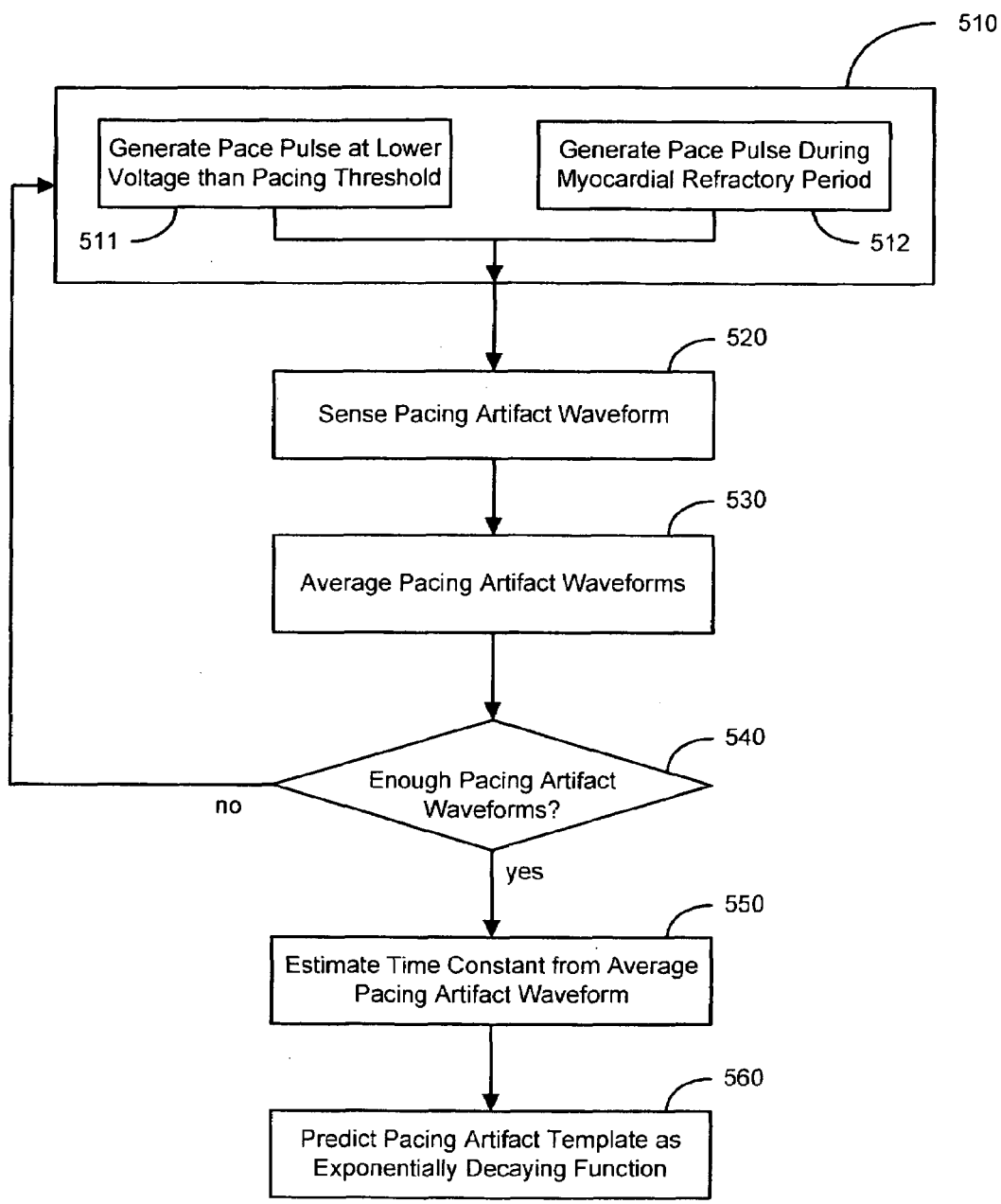
FIG. 5 is a flowchart illustrating a method predicting a pacing artifact template as an exponentially decaying function in accordance with an embodiment of the present invention.

FIG. 5 illustrates an alternative method of providing a pacing artifact template according to an embodiment of the present invention. The method described in the following paragraph, with reference to FIG. 5, may be used to provide a pacing artifact template at blocks 310, 720, 1010 and 1305 in FIGS. 3, 7, 10, and 13, respectively. A typical pacing artifact waveform in the cardiac verification window has a shape that can be approximated by an exponentially decaying function associated with a particular time constant. The time constant of an average pacing artifact waveform may be estimated and the pacing artifact template predicted using the estimated time constant.

In this exemplary embodiment, an average pacing artifact waveform is determined by sensing a predetermined number of pacing artifact waveforms generated by a predetermined number of pace pulses. As previously discussed, each pace pulse is delivered in such a way that capture does not occur, resulting in a pure pacing artifact waveform without a superimposed evoked response. The pace pulses may be delivered 511 at an energy level lower than the pacing threshold, for example. Alternatively, the pace pulses may be delivered 512 during a myocardial refractory period when the pace pulses cannot produce an evoked response.

Following delivery 510 of a pulse, the pacing artifact waveform is sensed 520 during a cardiac verification window. The pacing artifact waveform is averaged 530 with previously acquired pacing artifact waveforms. The process 510–530 of delivering a pulse and detecting the resultant pacing artifact waveform is repeated until the predetermined number of pacing artifact waveforms has been acquired 540.

When a sufficient number of pacing artifact waveforms has been acquired 540, a time constant of the average pacing artifact waveform is estimated 550. The pacing artifact template is predicted 560 as an exponentially decaying function using the estimated time constant. A pacing artifact template generated by either of the methods described in the preceding paragraphs with reference to FIGS. 4 and 5 may be periodically updated by acquiring additional pacing artifact waveforms and combining the additional pacing artifact waveforms with the pacing artifact template. For example, the additional pacing artifact waveforms may be combined with the pacing artifact template by averaging.

Figure 6:
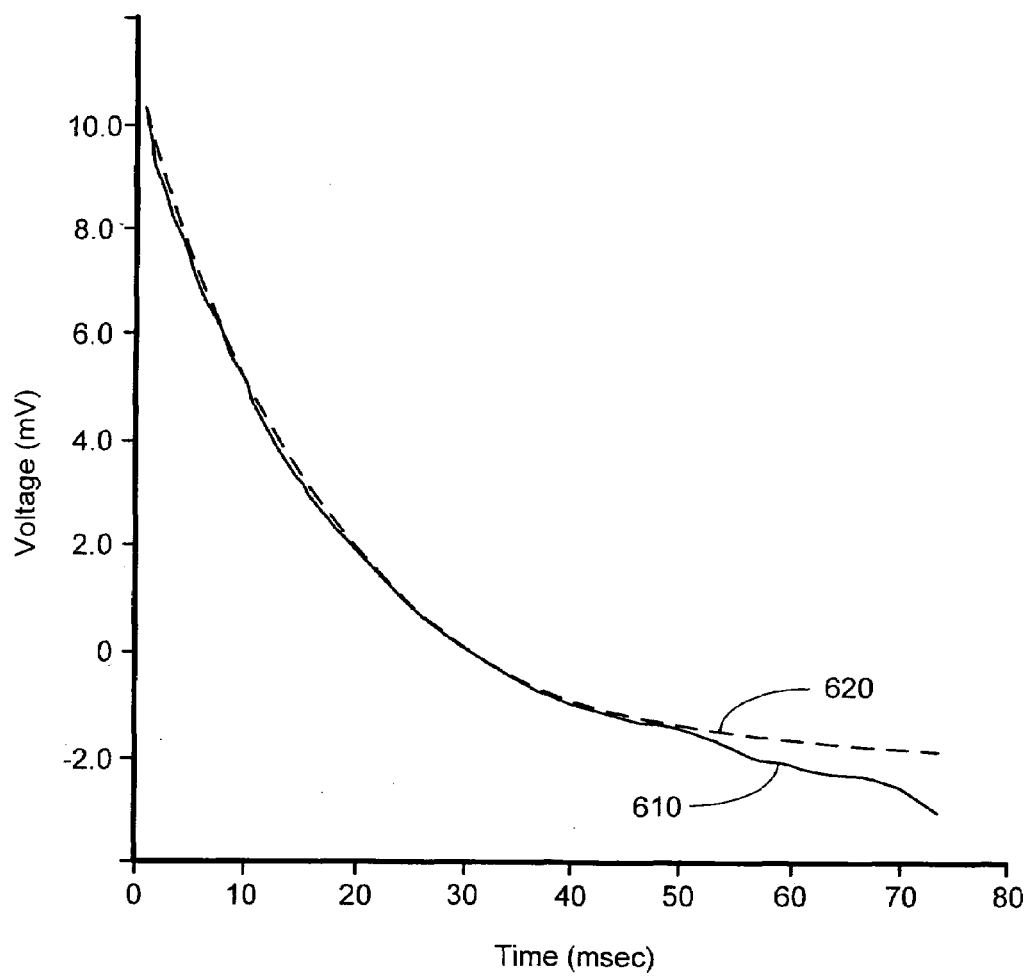
FIG. 6 is a graph comparing a measured pacing artifact with a pacing artifact predicted as an exponentially decaying function.

FIG. 6 shows a comparison of the actual pacing artifact template graph 610 and the pacing artifact template predicted as an exponentially decaying function 620. The pacing artifact template can be predicted for a sampled signal using Equation (1):

$$x(t)=A*x(t-1) \quad (1)$$

where $A=e^{-T/a}$ where x(t) represents a current sample of the pacing artifact template, x(t−1) represents a previous sample of the pacing artifact template, and A is a constant derived from the estimated time constant of the pacing artifact template, a, and the sample time, T.

According to one embodiment, a signal corresponding to the pacing artifact template may be generated by hardware using digital circuitry to produce the function of Equation (1). The pacing artifact template signal generated in hardware may be used to cancel the pacing artifact from a sensed cardiac signal in the capture verification window. In other embodiments, the pacing artifact template may be canceled from the sensed cardiac signal using software-based techniques. For example, the pacing artifact template may be canceled by subtracting stored values of the template from the sensed cardiac signal at each sample point.

Although the examples provided herein predict the pacing artifact using an exponential function, those skilled in the art will recognize that prediction of the pacing artifact is not limited to characterization by an exponential function. Any function or combination of functions may be used to characterize and predict the pacing artifact.

Figure 7:
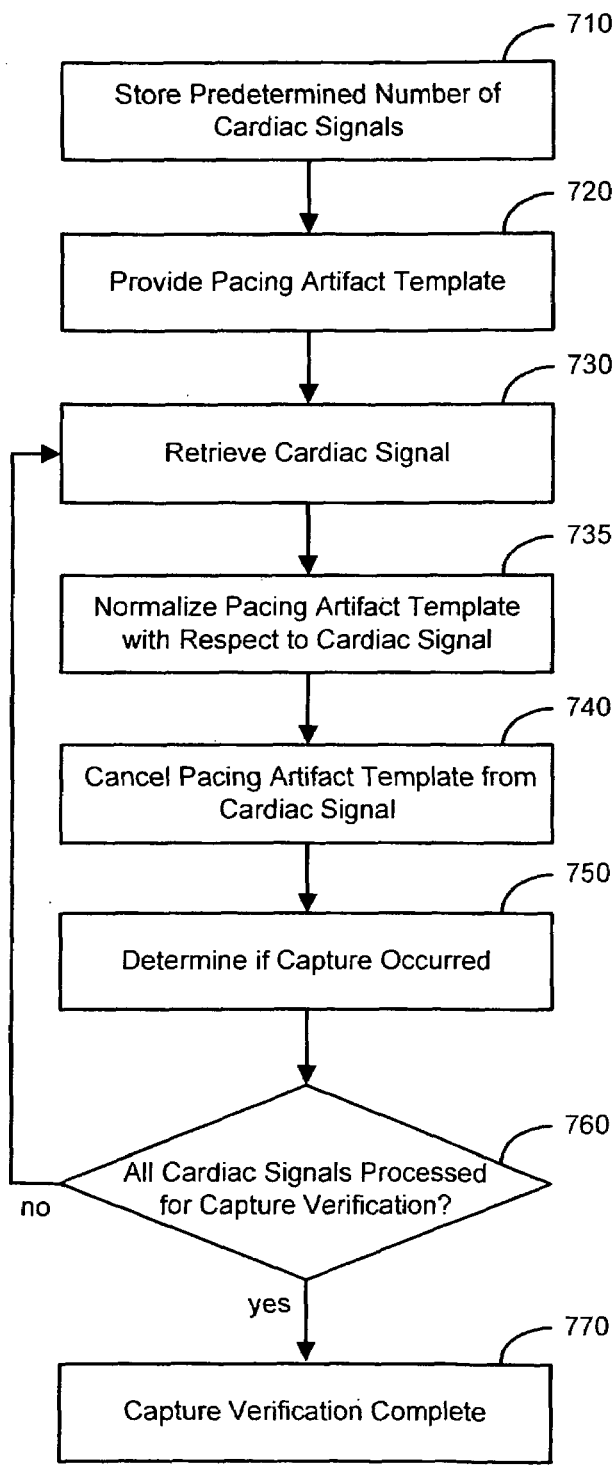
FIG. 7 is a flowchart illustrating a method of detecting capture on a batch basis in accordance with an embodiment of the present invention.

FIG. 7 illustrates a method of detecting capture by a batch process in accordance with an embodiment of the invention. A predetermined number of cardiac signals sensed following pace pulses are stored 710 in memory. Each cardiac signal is sensed during the cardiac verification window following the delivery of a pace pulse. The cardiac signals may represent a series of signals responsive to ramping down the pace pulse energy in a capture threshold determination procedure, for example. A pacing artifact template may be provided 720 by any of the methods previously discussed in connection with FIG. 4 or FIG. 5.

A previously stored cardiac signal is retrieved 730 from memory. The pacing artifact template is normalized 735 using one or more samples of the cardiac signal. In one example, one or more samples of the cardiac signal are averaged and the pacing artifact template normalized with respect to the average value. In another example, a representative set of the cardiac signal samples may be used to define a slope of the cardiac signal within the cardiac verification window. The pacing artifact template may be normalized with respect to a point extrapolated using the slope.

Figure 8B:
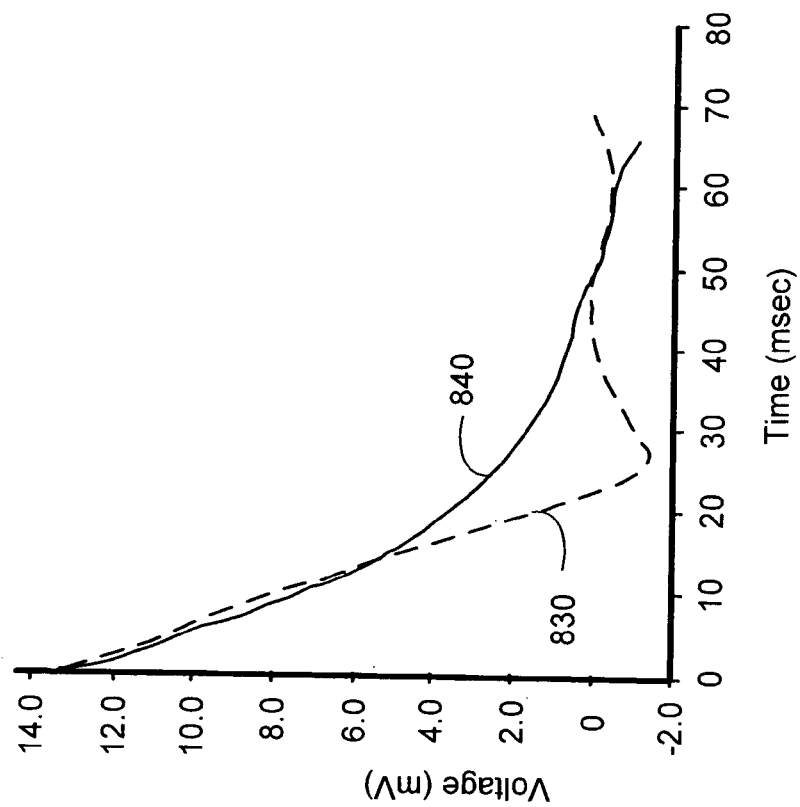
FIG. 8B is a graph comparing a captured evoked response template to a normalized pacing artifact template.
Figure 8A:
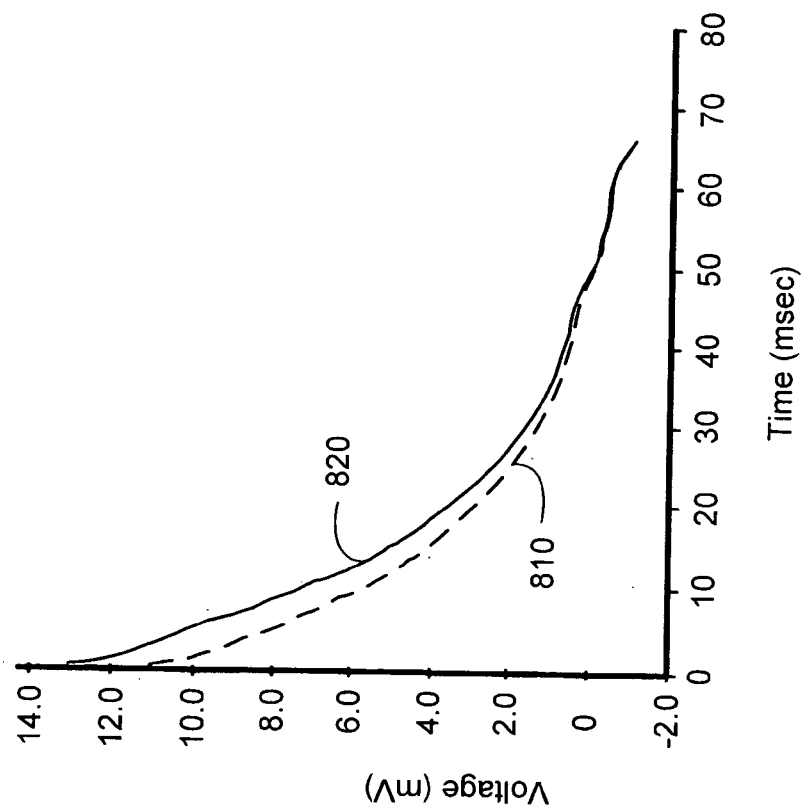
FIG. 8A is a graph illustrating normalization of a pacing artifact template in accordance with an embodiment of the invention.

Normalization of the pacing artifact template with respect to a first sample of the cardiac signal in the capture verification window is illustrated in FIGS. 8A and 8B. FIG. 8A shows a graph of a pacing artifact template before normalization 810 and after normalization 820 with respect to a sensed cardiac signal 830. FIG. 8B shows the graph of a normalized pacing artifact template 840 overlaying the graph of the sensed cardiac signal 830.

Returning now to FIG. 7, following normalization 735 of the pacing artifact template with respect to the sensed cardiac signal, the normalized pacing artifact template is canceled 740 from the cardiac signal. Capture is determined by analyzing the pacing artifact canceled cardiac signal 750. If additional cardiac signal waveforms remain to be processed for capture verification 760, the process described at blocks 730–750 is repeated until all of the cardiac signals have been processed and the capture verification process is complete 770 for all waveforms.

Figure 9:
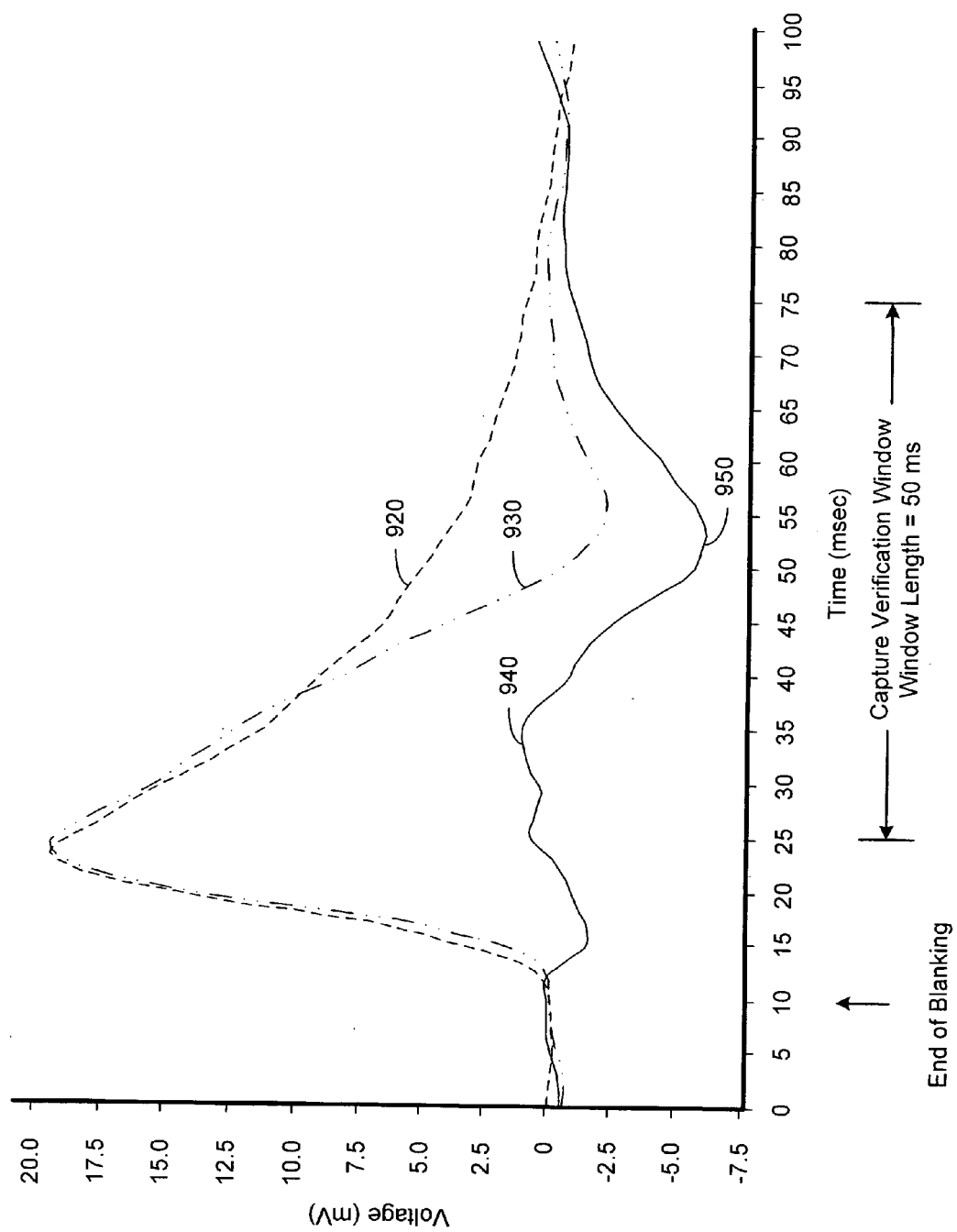
FIG. 9 is a graph comparing a captured and non-captured waveform in a capture verification window.

Cancellation of a pacing artifact template from a sensed cardiac signal in accordance with the invention is illustrated in FIG. 9. A capture verification window commences approximately 25 ms following delivery of the pacing pulse and extends for approximately 50 ms. The pacing artifact template 920 is shown overlaying the sensed cardiac waveform of a captured beat 930. Cancellation of the pacing artifact template 920 from the sensed cardiac waveform 930 results in a pacing artifact canceled waveform 940 from which capture is determined. In the example of FIG. 9, capture is indicated by the presence of the local minima 950 at approximately 53 ms following the pace pulse.

Figure 10:
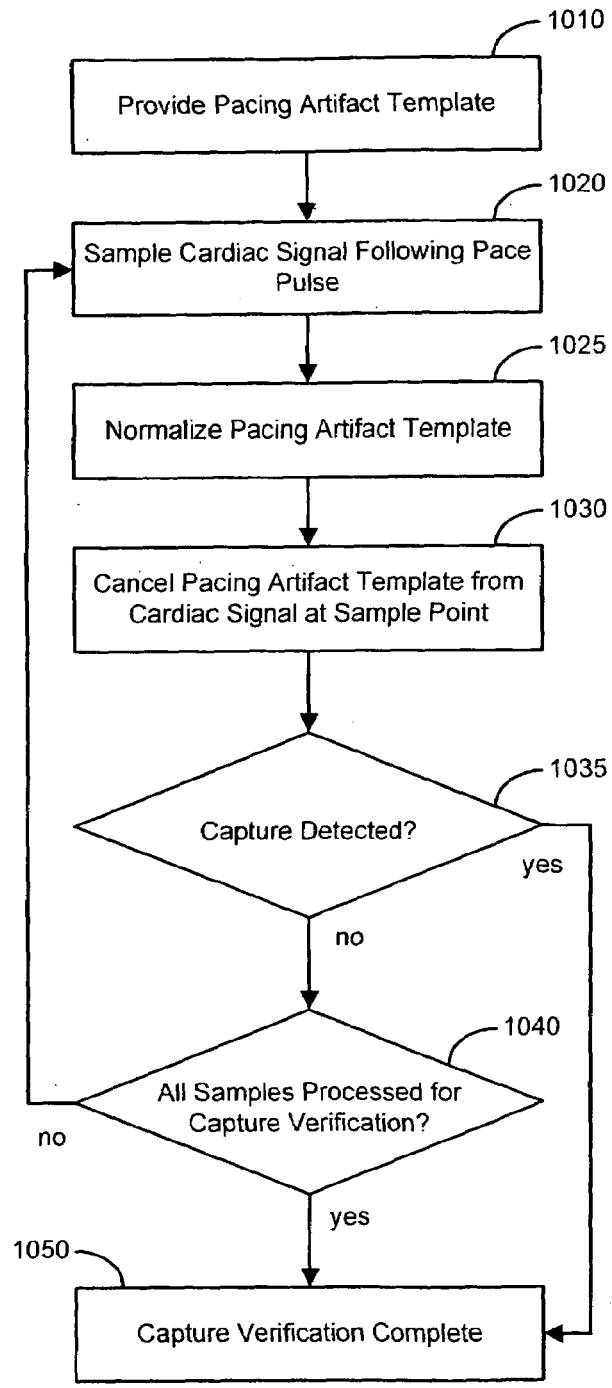
FIG. 10 is a flowchart of a method of detecting capture on a beat by beat basis in accordance with an embodiment of the present invention.

Turning now to FIG. 10, a method of detecting capture on a sample by sample basis in accordance with an embodiment of the invention is illustrated. A pacing artifact template is provided 1010 by either of the methods previously discussed in connection with FIGS. 4 and 5. A cardiac signal following a pace pulse is sampled 1020. The pacing artifact template is normalized 1025 with respect to the first sample of the cardiac signal. The pacing artifact template is canceled 1030 from the cardiac signal at each sample point. The loop described by blocks 1020–1030 continues until all samples of the cardiac signal have been processed 1040 or until capture is detected 1035 and capture verification is complete 1050.

As previously discussed, fusion or pseudofusion may occur during pacing. A fusion beat occurs when an intrinsic cardiac depolarization of a particular chamber merges with a pacer output pulse within that chamber. Pseudofusion occurs when a pacer output pulse artifact is superimposed upon a spontaneous P wave during atrial pacing, or upon a spontaneous QRS complex during ventricular pacing. In pseudofusion, the pacing stimulus is ineffective because the tissue around the electrode has already spontaneously depolarized and is in its refractory period. During a capture verification procedure, it may be desirable to detect fusion and pseudofusion beats to prevent false capture detection.

A method of detecting fusion/pseudofusion beats in accordance with the present invention relies upon canceling a template representative of a captured response from a sensed cardiac waveform and examining the resultant waveform. The captured response template includes two superimposed component signals, an evoked response and a pacing artifact response. The evoked response component represents the cardiac signal associated with contraction of the heart tissue in response to the pace pulse. The pacing artifact component represents the post pace residual polarization waveform. A fusion/pseudofusion beat may be discriminated from a captured response beat based on beat waveform morphology characteristics. For example, a fusion/pseudofusion beat may have a larger peak amplitude when compared to a captured response, allowing the fusion/pseudofusion beat to be detected.

Figure 11:
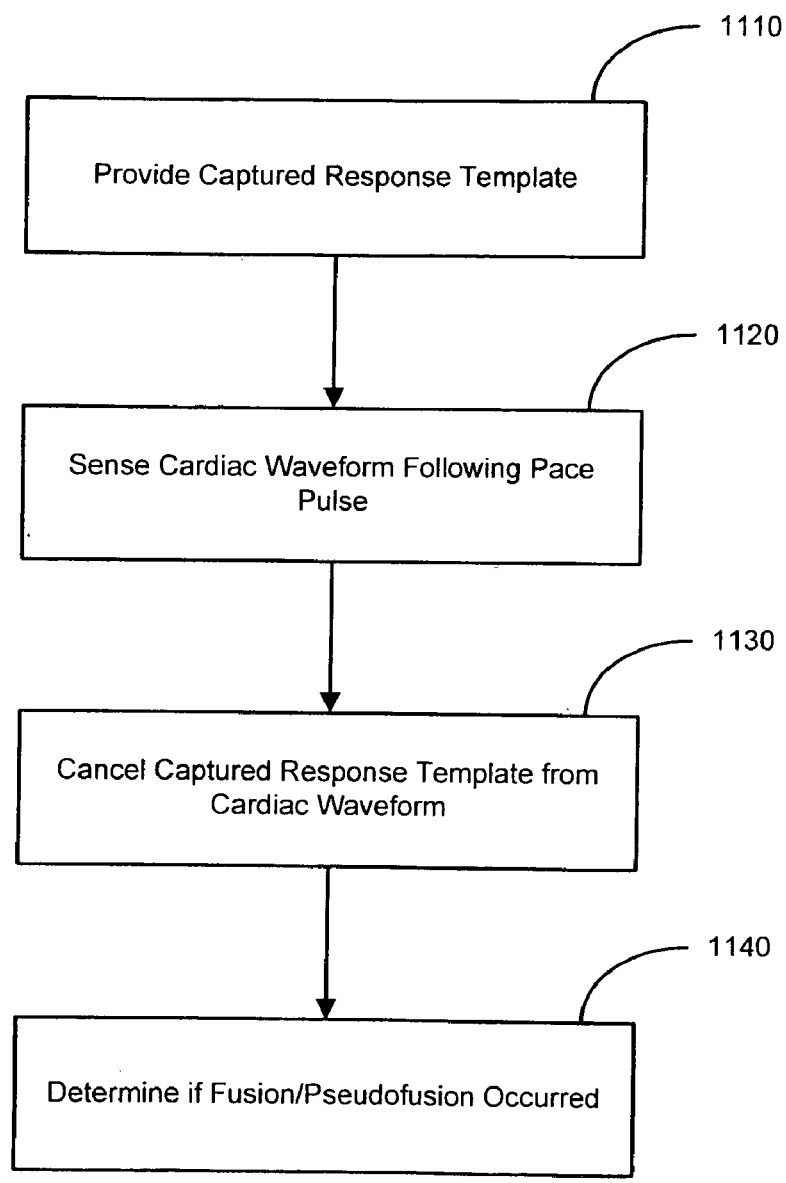
FIG. 11 is a flowchart conceptually illustrating a method of detecting fusion/pseudofusion in accordance with an embodiment of the present invention.

A method of fusion/pseudofusion detection in accordance with an embodiment of the present invention is illustrated in FIG. 11. A captured response template is provided 1110 which is representative of a captured beat waveform within a fusion/pseudofusion detection window. The fusion/pseudofusion detection window may begin, for example, at the end of a blanking period and extend for approximately 20 ms. A blanking period of approximately 10 ms may follow a pace pulse during which sensing is inhibited to prevent erroneous sensing of a cardiac response. A cardiac waveform is sensed 1120 in the fusion/pseudofusion detection window following a pace pulse. The captured response template is canceled 1130 from the sensed cardiac waveform. Fusion/pseudofusion is determined 1140 by analyzing the waveform resulting from the cancellation of the captured response template from the sensed cardiac waveform.

Providing a captured response template may also encompass periodically updating the captured response template. The captured response template may be periodically updated by averaging a captured response waveform with the existing captured response template.

Figure 12A:
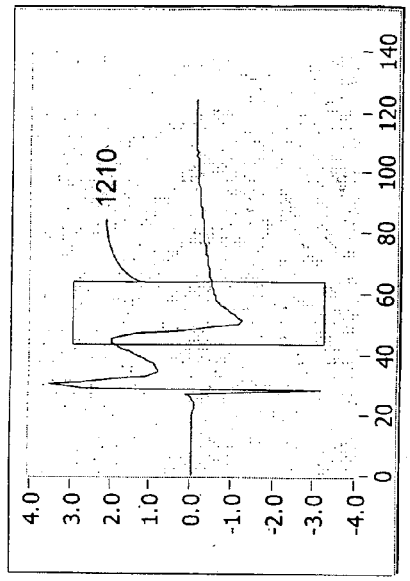
FIGS. 12A–12D are graphs illustrating a method fusion/pseudofusion detection window in accordance with an embodiment of the invention.
Figure 12B:
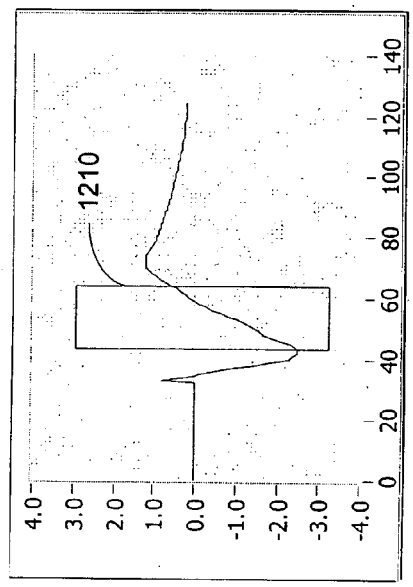
Figure 12C:
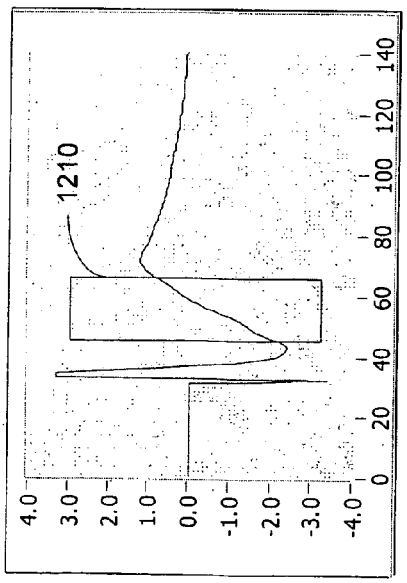
Figure 12D:
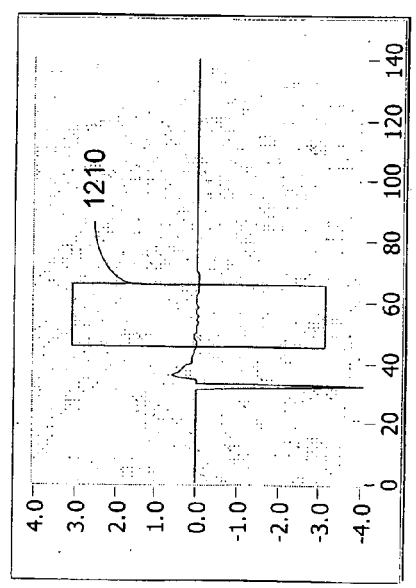

FIGS. 12A–D are graphs illustrating detection of a pseudofusion beat in accordance with an embodiment of the invention. FIGS. 12A and 12B illustrate a graph of a captured response template without fusion/pseudofusion, and the graph of a pseudofusion beat, respectively. FIGS. 12C and 12D illustrate the captured response signal and a pseudofusion beat after cancellation of the captured response template. Pseudofusion may be detected by comparing the captured response template canceled captured beat in FIG. 12C and the captured response template canceled pseudofusion beat in FIG. 12D in the fusion/pseudofusion detection window 1210.

Figure 13:
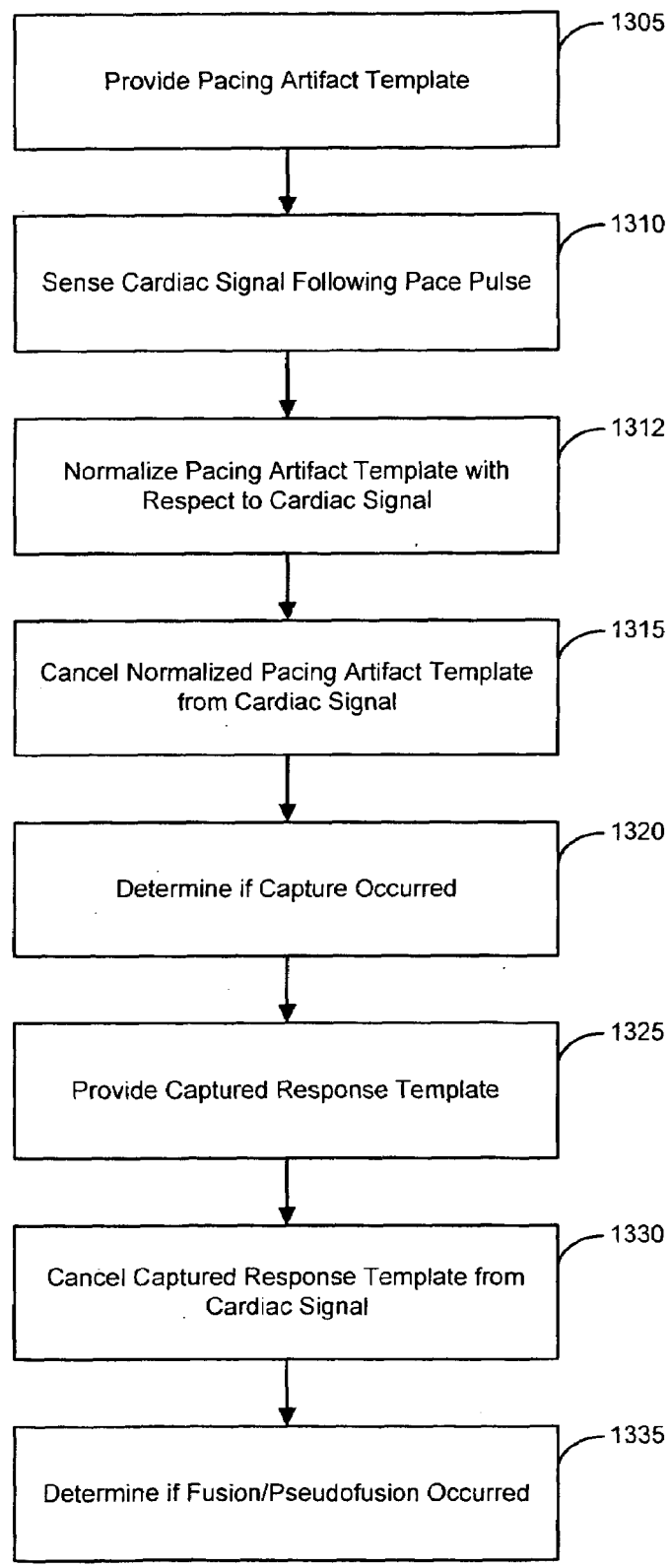
FIG. 13 is a flowchart conceptually illustrating a method of detecting capture and fusion/pseudofusion in accordance with an embodiment of the present invention.

FIG. 13 is a flowchart illustrating capture verification, including fusion/pseudofusion detection in accordance with the present invention. A pacing artifact template is provided 1305, for example, by one of the methods discussed in the previous paragraphs with reference to FIGS. 4 and 5. Following generation of a pace pulse, a cardiac signal is sensed 1310 during a cardiac verification window. The pacing artifact template is normalized 1312 with respect to the cardiac signal and the pacing artifact template is canceled 1315 from the cardiac signal. Capture is determined 1320 using the pacing artifact canceled cardiac signal.

A captured response template is provided 1325 that is representative of a captured beat. The captured response template is canceled 1330 from the cardiac signal in the fusion/pseudofusion detection window and fusion/pseudofusion is determined 1335 from analysis of the resultant waveform.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for detecting capture in a patient's heart comprising:
   providing, in an implantable device, a pacing artifact template by estimating a time constant of a pacing artifact signal and forming the pacing artifact template in terms of an exponential function using the estimated time constant;
   sensing a cardiac signal following a pacing pulse;
   canceling the pacing artifact template from the cardiac signal; and detecting capture using the pacing artifact canceled cardiac signal.

2. The method of claim 1, wherein the artifact template is associated with a pacing energy used for the pace pulse.

3. The method of claim 1, wherein providing the pacing artifact template further comprises periodically updating the pacing artifact template.

4. The method of claim 1, wherein canceling the pacing artifact template from the cardiac signal further comprises normalizing the pacing artifact template.

5. The method of claim 1, wherein the cardiac signal is sensed in a cardiac verification window.

6. The method of claim 5, wherein the cardiac verification window is defined by a time interval beginning at a first predetermined time following a pacing pulse and continuing for a second predetermined time.

7. The method of claim 6, wherein the first predetermined time is about 25 ms and the second predetermined time is about 50 ms.

8. The method of claim 1, wherein providing the pacing artifact template comprises:
   delivering one or more pace pulses to the heart, wherein the pace pulses do not produce capture;
   sensing one or more pacing artifact waveforms produced by the one or more pace pulses;
   averaging the one or more pacing artifact waveforms to form an average pacing artifact waveform; and forming the pacing artifact template using the average pacing artifact waveform.

9. The method of claim 8, wherein each pace pulse is generated at a voltage lower than a pacing threshold.

10. The method of claim 8, wherein each pace pulse is generated during a myocardial refractory period.

11. The method of claim 8, wherein delivering the one or more pace pulses to the heart comprises delivering the one or more pace pulses to the heart at a particular energy level.

12. The method of claim 8, wherein delivering the one or more pace pulses to the heart comprises delivering the one or more pace pulses to the heart at a particular range of energy levels.

13. The method of claim 8, wherein each of the one or more pacing artifact waveforms is sensed in a cardiac verification window.

14. The method of claim 13, wherein the cardiac verification window is defined by a time interval beginning at a first predetermined time following a pacing pulse and continuing for a second predetermined time.

15. The method of claim 14, wherein the first predetermined time is about 25 ms and the second predetermined time is about 50 ms.

16. The method of claim 1, wherein providing the pacing artifact template comprises providing one or more pacing artifact templates.

17. The method of claim 16 wherein:
   providing the one or more pacing artifact templates comprises providing each of the one or more pacing artifact templates respectively associated with a different pacing energy; and
   canceling the pacing artifact template comprises:
      selecting a pacing artifact template of the one or more pacing artifact
      templates, the selected pacing artifact template associated with a pacing energy of the pacing pulse: and
      canceling the selected pacing artifact template from the cardiac signal.

18. The method of claim 1, wherein providing the pacing artifact template comprises forming the pacing artifact template in terms of a combination of one or more exponential functions.

19. The method of claim 1, wherein providing the pacing artifact template comprises:
   producing a plurality of pacing artifact waveforms; averaging the plurality of pacing artifact waveforms to form an average pacing artifact waveform; and
   estimating the time constant from the average pacing artifact waveform.

20. The method of claim 19, wherein the time constant is estimated from the average pacing artifact waveform in a predetermined time interval.

21. The method of claim 19, wherein producing the plurality of pacing artifact waveforms comprises:
   generating one or more pacing pulses; and
   sensing the one or more pacing artifact waveforms produced by the one or more pacing pulses.

22. The method of claim 21, wherein each pacing pulse is generated at an energy level lower than a pacing threshold.

23. The method of claim 21, wherein each pacing pulse is generated during a myocardial refractory period.

24. The method of claim 21, wherein each of the plurality of pacing artifact waveforms is sensed in a cardiac verification window.

25. The method of claim 24, wherein the cardiac verification window begins at a first predetermined time following a pacing pulse and continues for a second predetermined time.

26. The method of claim 25, wherein the first predetermined time is about 25 ms following the pacing pulse.

27. The method of claim 25, wherein the second predetermined time is about 50 ms.

28. The method of claim 1, wherein detecting capture comprises detecting capture during a capture threshold test.

29. The method of claim 28, wherein detecting capture during the capture threshold test further comprises:
sensing a plurality of cardiac signals;
for each cardiac signal, forming the pacing artifact template by estimating the time constant of the pacing artifact signal; and
detecting capture for each cardiac signal during the capture threshold test using the pacing artifact template formed for the cardiac signal.

30. The method of claim 1, wherein detecting capture comprises detecting capture on a beat by beat basis.

31. A medical device for detecting capture in a patient's heart, comprising:
a lead system, the lead system comprising electrodes and extending into the heart;
pulse generator circuitry coupled to the lead system for providing pulses to the heart;
sensing circuitry, the sensing circuitry coupled to the lead system and configured to sense cardiac signals transmitted through the lead electrodes;
a control system configured to control the operation of the device including the sense circuitry and the pacemaker circuitry; and
a capture detection system coupled to the sensing circuitry and the control system and configured to provide a pacing artifact template by estimating a time constant of a pacing artifact signal and forming the pacing artifact template in terms of an exponential function using the estimated time constant, cancel a the pacing artifact template from the a sensed cardiac signals-signal, and determine if capture occurs using the pacing artifact canceled cardiac signal.

32. The medical device of claim 31, further comprising a switching matrix configured to connect leads from a particular heart chamber to the sensing circuitry for determining capture in the particular heart chamber.

33. The medical device of claim 31, wherein the capture detection system further includes circuitry configured to cancel the pacing artifact template from the sensed cardiac signal using a hardware based implementation.

34. The medical device of claim 31, wherein the capture detection system further includes circuitry configured to cancel the pacing artifact template from the sensed cardiac signal using a hardware based implementation.

35. The medical device of claim 31, wherein the capture detection system is configured to periodically update the pacing artifact template.

36. The medical device of claim 31, wherein the capture detection circuitry is configured to normalize the pacing artifact template.

37. The medical device of claim 31, wherein the cardiac signals are detected during a capture verification window.

38. The medical device of claim 31, wherein the capture detection system is configured to form a plurality of pacing artifact templates.

39. The medical device of claim 38, wherein the each pacing artifact template of the plurality of pacing artifact templates is respectively associated with a distinct pacing energy.

40. The medical device of claim 39, wherein the capture detection circuitry is configured to select a pacing artifact template associated with a pacing energy of the pacing pulse and to cancel the selected pacing artifact template from the cardiac signal.

41. The medical device of claim 38, wherein the estimated pacing artifact template is estimated using the equation:

$$x(t)=A*x(t-1),$$

where $A=e^{-T/a}$ where x(t) represents a current sample of the estimated pacing artifact signal, x(t−1) represents a previous sample of the estimated pacing artifact signal, and A is a constant derived from a time constant of the pacing artifact template, a, and a sample time, T, of the cardiac signals.

42. A system for detecting capture, comprising:
means for providing, in an implantable device, at least one pacing artifact template by estimating a time constant of a pacing artifact and forming the at least one pacing artifact template in terms of an exponential function using the estimated time constant;
means for sensing a cardiac signal;
means for canceling the at least one pacing artifact template from the cardiac signal; and
means for determining if capture occurs using the pacing artifact canceled cardiac signal.

* * * * *